United States Patent [19]
Fleetwood

[11] Patent Number: 5,520,665
[45] Date of Patent: May 28, 1996

[54] CONNECTING APPARATUS FOR MEDICAL CONDUITS

[75] Inventor: Antony Fleetwood, King's Lynn, United Kingdom

[73] Assignee: Bespak Plc, Norfolk, England

[21] Appl. No.: 211,680

[22] PCT Filed: Aug. 27, 1993

[86] PCT No.: PCT/GB93/01828

§ 371 Date: Sep. 8, 1994

§ 102(e) Date: Sep. 8, 1994

[87] PCT Pub. No.: WO94/05366

PCT Pub. Date: Mar. 17, 1994

[30] Foreign Application Priority Data

Sep. 7, 1992 [GB] United Kingdom ............... 9218912

[51] Int. Cl.⁶ .................................................. A61M 25/00
[52] U.S. Cl. ........................ 604/283; 604/246; 604/249; 604/905
[58] Field of Search ........................ 604/246, 249, 604/256, 283, 905

[56] References Cited

U.S. PATENT DOCUMENTS

| | | | |
|---|---|---|---|
| 4,334,551 | 6/1982 | Pfister | 137/614.03 |
| 4,745,950 | 5/1988 | Mathieu | 604/905 X |
| 4,758,225 | 7/1988 | Cox et al. | 604/126 |
| 4,842,591 | 6/1989 | Luther | 604/283 |
| 4,917,668 | 4/1990 | Haindl | 604/167 |
| 5,103,868 | 4/1992 | Wilkins | 137/614.03 |
| 5,108,380 | 4/1992 | Herlitze et al. | 604/283 |
| 5,215,538 | 6/1993 | Larkin | 604/249 |
| 5,269,771 | 12/1993 | Thomas et al. | 604/213 |

FOREIGN PATENT DOCUMENTS

| | | |
|---|---|---|
| 408082 | 4/1934 | United Kingdom . |
| 837425 | 6/1960 | United Kingdom . |
| 2067075 | 7/1981 | United Kingdom . |
| 2116277 | 9/1983 | United Kingdom . |

Primary Examiner—Corrine M. McDermott
Attorney, Agent, or Firm—Beveridge, DeGrandi, Weilacher & Young

[57] ABSTRACT

A connecting apparatus for medical conduits including a valve body defining a first duct and having a connector for coupling to a first conduit. A valve is incorporated within the first duct and is a ball and spring type valve normally biased in closed position. An adaptor is releasably connectable to the body and has a female coupling for connection to a second conduit having a male coupling. A valve actuator is received within the adaptor and is arranged such that by connecting the adaptor to the valve body and then connecting the second conduit to the adaptor, the male coupling automatically moves the valve actuator towards the valve member thereby opening the valve against the action of the spring. When the adaptor is disconnected from the valve body, the valve member assumes a closed position in which an exposed surface portion of the spherical valve member is substantially flush with the end face of the valve body. The apparatus is suitable for connecting medical conduits such as those used in intravenous delivery.

10 Claims, 4 Drawing Sheets

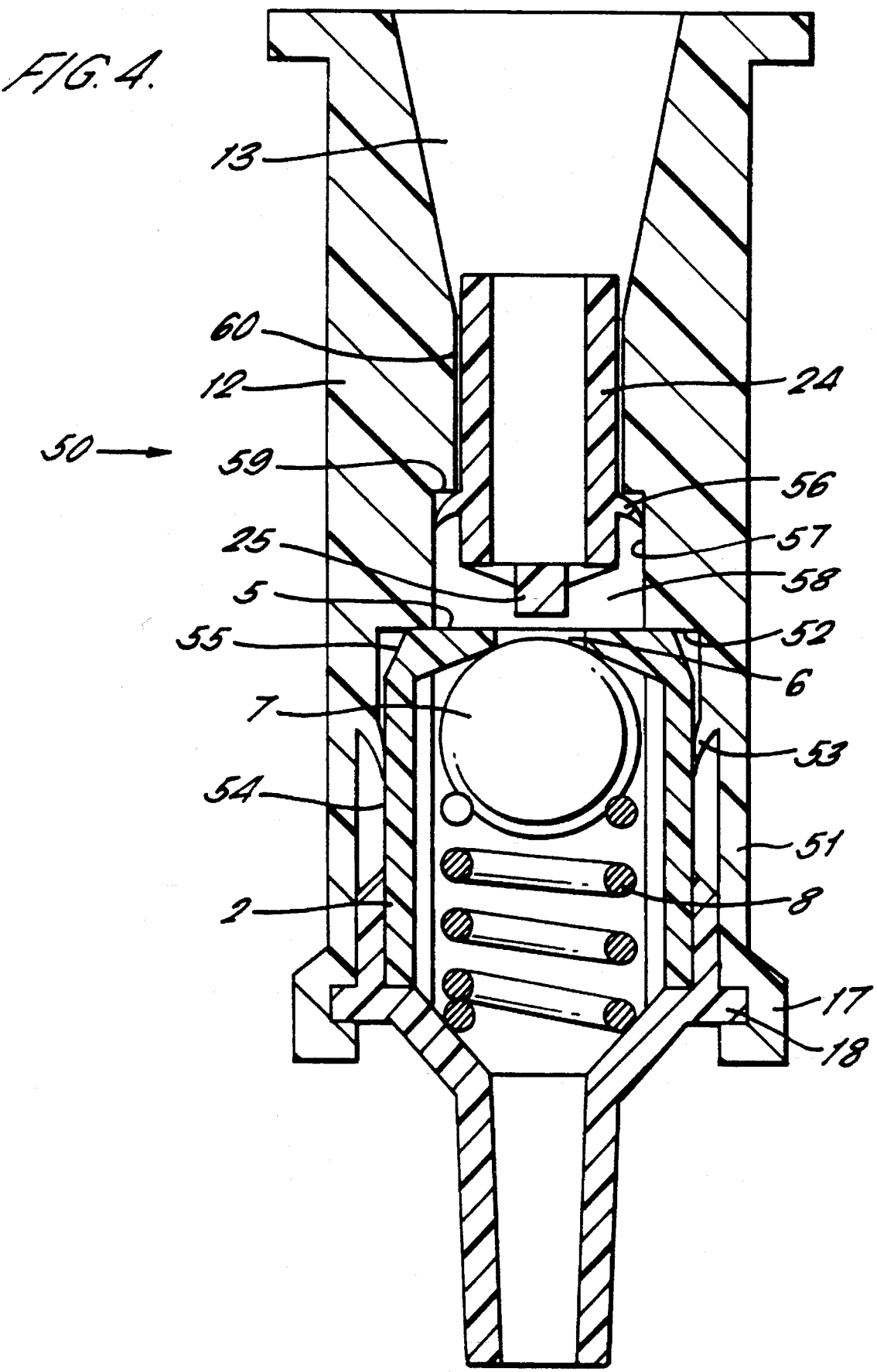

CONNECTING APPARATUS FOR MEDICAL CONDUITS

This invention relates to connecting apparatus for connecting medically used conduits and in particular but not exclusively to connecting apparatus for use in the intravenous delivery of liquids.

It is known to provide connecting apparatus for joining end-to-end conduits in a delivery line, a first conduit typically being connected to the patient by a cannulation device and a second conduit being attached to a source of liquid.

It is a common requirement to be able to disconnect the first and second conduits from one another when changing to a new source of liquid and typically a new second conduit is then to be presented for connection to the first conduit. It is highly desirable for this connection process to be simple and to avoid the ingress of air into the conduits since the presence of air is hazardous to the patient. The ingress of air is a particular problem where the connection is to be made upstream of an infusion pump such that a degree of suction is developed within the first conduit. A commonly used form of connector employs a valve mechanism to seal the first conduit during periods in which it is disconnected from the second conduit and typically a valve mechanism is provided of a type in which a needle penetrates a septum to provide liquid communication in the open condition of the valve.

The disadvantage of such valves is that there is an associated hazard in using such needles in that the operative may sustain injury during handling the apparatus or there may be a hazard associated with incorrect disposal after use.

It is also desirable for the connecting apparatus to be provided with a valve mechanism which can be readily cleansed of any residual liquid after disconnection of the conduits to avoid bacterial growth which could contaminate infusion liquid when the conduits are reconnected.

The valve mechanism should also preferably be suited to preventing the ingress of air when suction is developed within the first conduit. Certain types of valve such as duckbill valves are therefore unsuitable for this purpose.

According to the present invention there is disclosed apparatus for connecting medical conduits comprising a valve body defining a first duct and having first connecting means for connecting a first conduit in communication with the first duct, the valve body comprising a valve having a valve member and biassing means which biasses the valve member into a position in which it closes a mouth of the first duct, an adaptor defining a second duct and having a female coupling for connecting a second conduit having a co-operating male coupling in communication with the second duct, connector means operable to releasably connect the valve body and the adaptor such that the mouth of the first duct is presented to a mouth of the second duct, and a valve actuator located within the second duct and movably engageable with the valve member when the valve body and adaptor are operatively connected, wherein the valve actuator is displaceable relative to the adaptor by insertion of the male coupling into operative engagement with the female coupling so as to move the valve member into a position in which the valve is opened.

An advantage of such an arrangement is that it does not involve the use of a needle and is therefore inherently safe.

Preferably the valve member includes an exposed surface portion which, when the adaptor is separated from the valve body, is exposed via the mouth of the first duct and wherein the exposed surface portion is convex so as to project at least partially through the mouth of the first duct.

An advantage of such an arrangement is that it avoids the formation of any recess in the region of the mouth of the first duct which might otherwise result in the accumulation of congealed liquid after the separation of the adaptor from the valve body. It also makes possible the cleaning of the exposed surface portion.

The valve member may be spherical and typically may be a stainless steel ball.

The valve member may alternatively be formed of an elastomeric material and may be generally cylindrical in shape with a conically tapering surface projecting through the mouth of the first duct.

Preferably the mouth of the first duct is formed in an end face of a first end of the valve body and the end face is substantially free of projections and indentations.

This simplifies cleaning and avoids the accumulation of congealed liquid.

Preferably the end face is planar.

Conveniently the apparatus comprises limiting means operable to limit travel of the actuator relative to the adaptor. The limiting means may be provided by a radial projection of the actuator and a cooperating axially extending groove of the adaptor.

Preferably the adaptor is provided with an annular seal operable to provide a continuous seal peripheral to the mouth of the first duct between the actuator and the end face of the valve body.

Preferably the seal is also operable to provide a continuous seal peripheral to the second duct between the actuator and the adaptor.

Alternatively the actuator may be provided with an integral annular seal member projecting radially into slidable sealing engagement with the adaptor and the adaptor may be provided with a bore receiving the actuator, the bore having a stepped diameter defining an annular shoulder cooperable with the annular seal member to constitute the limiting means.

Conveniently the apparatus comprises a further annular seal member formed integrally with the valve body or the adaptor and operable to provide a seal between an external cylindrical surface of the valve body and an internal cylindrical surface of the adaptor.

Specific embodiments of the present invention will now be described by way of example only and with reference to the accompanying drawings of which:

FIG. 4 is a longitudinal section of a further alternative apparatus in accordance with the present invention.

Figure 1:
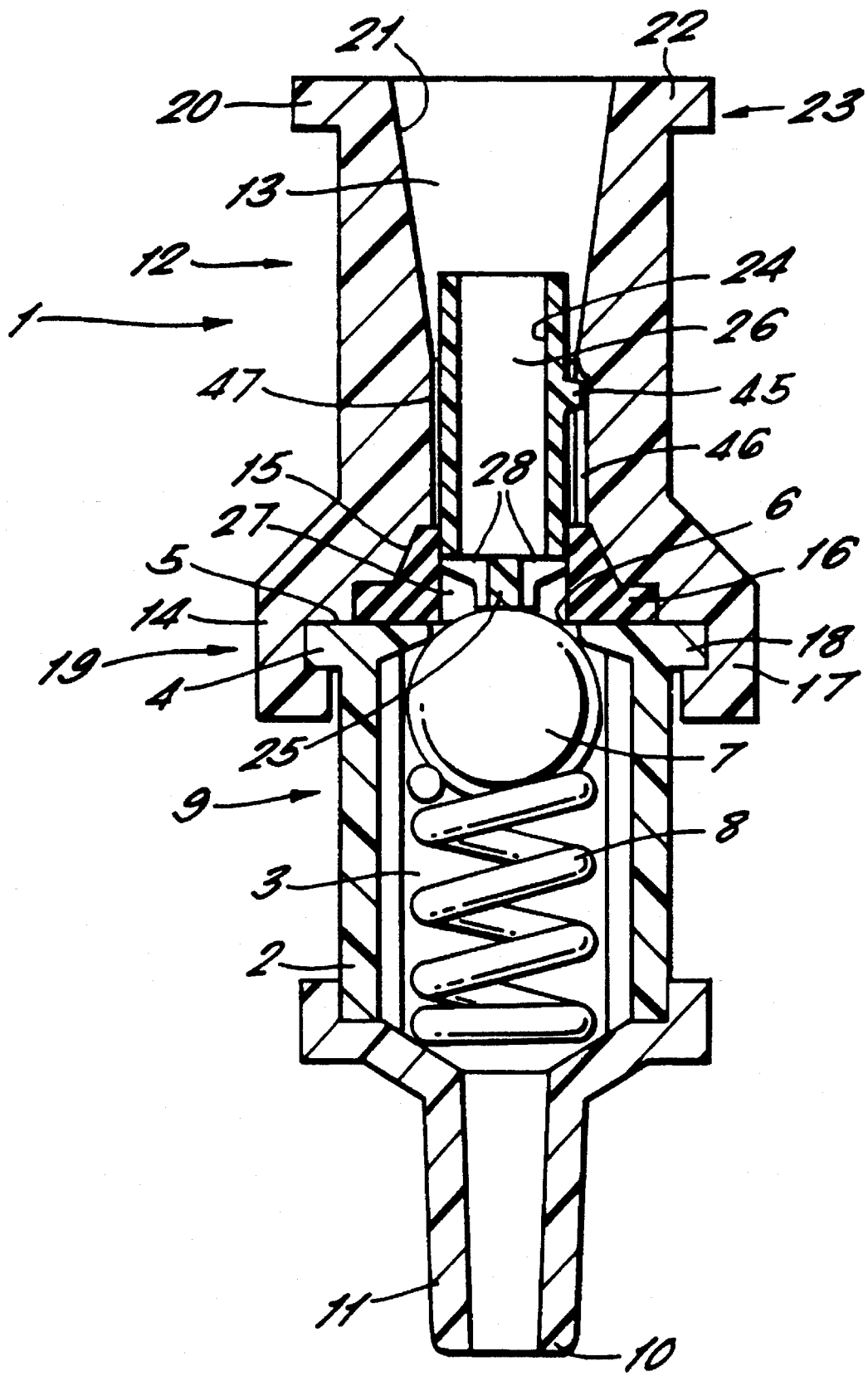
FIG. 1 is a longitudinal section through an apparatus in accordance with the present invention showing the valve in the closed position and the female coupling prior to insertion of the male coupling.

In FIG. 1 an apparatus 1 includes a generally tubular valve body 2 of a plastics material which defines a first duct 3. A first end 4 of the valve body 2 has a planar end face 5 in which is centrally formed a circular aperture 6 constituting a mouth of the first duct 3.

A spherical stainless steel valve member 7 is located within the first duct 3 and is biassed by a coil compression spring 8 with the first duct 3 into a position in which it normally obturates the aperture 6. The valve member 7, spring 8 and aperture 6 thereby constitute a valve 9 which is closed as shown in FIG. 1 thereby preventing the flow of liquid through the first duct 3.

The valve body 2 has a second end 10 of reduced external diameter defining a tubular sleeve 11 which constitutes means for connecting a tube of plastic material defining a first conduit (not shown in FIG. 1) through which liquid is to be delivered to a patient. The first conduit typically forms one branch of a Y connector having a second branch connected to a liquid supply, the Y connector being connected with the inlet of an infusion pump so that a degree of suction is developed within the first conduit. Such an arrangement is suited to situations where a continuous supply of liquid is infused and an intermittent supply is to be connected via the first conduit.

The apparatus 1 further comprises an adaptor 12 which is generally tubular and defines a second duct 13. The adaptor 12 has a first end portion 14 having a flared aperture 15 communicating with the second duct 13 and receiving an annular elastomeric seal 16.

The first end portion 14 is provided peripherally with female connecting formation 17 which is co-operable with male connection formations 18 provided on the first end 4 of the valve body 2. The connection formations 17 and 18 constitute connector means 19 which releasably connect the valve body 2 to the adaptor 12 such that the end face 5 of the valve body 2 is sealed to the adaptor by the annular seal 16 at a location peripheral to the aperture 6.

The adaptor 12 has a second end portion 20 defining a conically tapered internal surface 21 and an external coupling formation 22 which together provide a female coupling 23.

A valve actuator 24 of generally tubular shape is axially slidably received within the second duct 13 and has a leading end portion 25 which projects axially from the valve actuator into contact with the valve member 7. The actuator 24 has a radial projection 45 which locates in an axially extending groove 46 which is provided on a cylindrical internal surface 47 of the adaptor 12. The axial extent of the groove 46 is such as to provide limited axial movement of the valve actuator 24. The valve actuator 24 defines an internal passageway 26 which extends axially and communicates with an annular space 27 surrounding the leading end portion 25 via circumferentially spaced ports 28 which are formed adjacent to the leading end portion. The actuator is peripherally sealed to the adaptor 12 by sliding contact with the seal 16.

Figure 2:
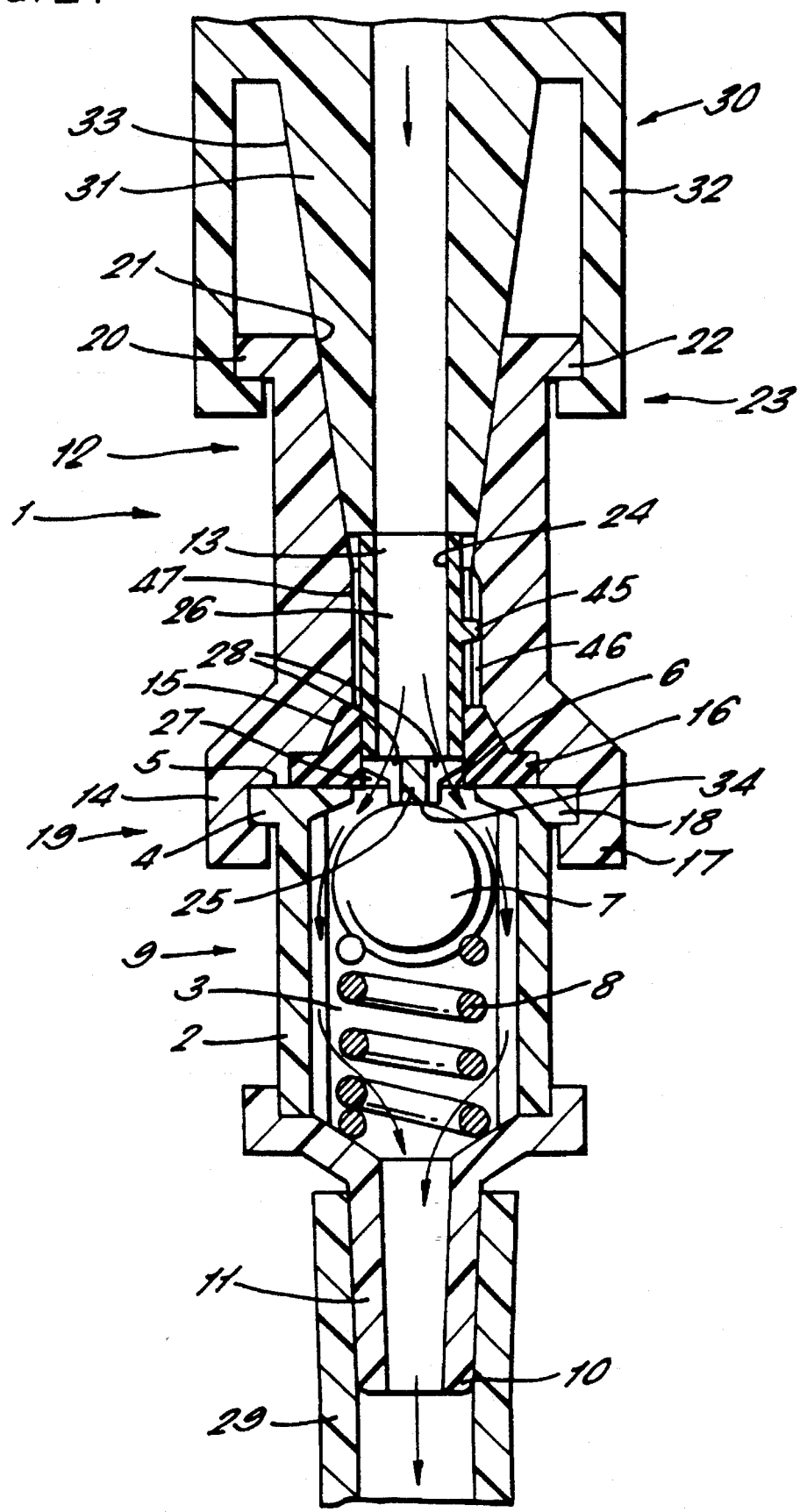
FIG. 2 is a longitudinal section of the apparatus of FIG. 1 showing the valve in the open position in which the male coupling is operatively engaged with the female coupling.

In FIG. 2 the apparatus 1 is shown with a first conduit 29 connected to the sleeve 11 for the delivery of liquid to a patient.

A male coupling 30 is connected to a second conduit (not shown) which is connected with a supply of liquid (not shown) comprises an insertion member 31 and a locking member 32. The male coupling has an internal bore corresponding in aperture to the passageway 26.

The insertion member 31 has a conically tapering external surface 33 which is sealingly engaged with the tapered internal surface 21 of the adaptor 12.

The locking member 32 engages the coupling formation 22 of the adaptor 12, the male coupling 30 being moved into this locked position by inserting the insertion member 31 into the second duct 13 and rotating the male coupling 30 to lock the locking member 32 on to the coupling formation 22.

During insertion to this fully inserted coupled position as shown in FIG. 2 the valve actuator 24 is moved axially from its initial rest position as shown in FIG. 1 into an actuated position. In this actuated position the valve member 7 is depressed by compression of the spring 8 into a position in which it no longer obturates the aperture 6. The valve 9 is therefore opened and in this position the first duct 3 is placed in communication with the second duct 13 via the aperture 6. Movement of the valve actuator 24 continues until the external surface 33 of the insertion member 31 makes sealing engagement with the internal surface 21 of the adaptor 12. During a last portion of this travel of the valve actuator 24 the valve 9 progressively opens before sealing contact is made between the insertion member 31 and the adaptor 12 but the ingress of air into the internal passageway 26 of the valve actuator 24 is prevented by continuous circumferential contact with the insertion member 31 which makes end to end contact with the actuator. Any suction developed within the first conduit is therefore communicated to the second conduit during this phase of insertion rather than allowing ambient air to be drawn into the first conduit.

In use the adaptor 12 is connected to the valve body 2 by the connector means 19 and the male coupling 30 is then coupled to the female coupling 23 thereby moving the actuator 24 and opening the valve 9. Liquid flowing through the second conduit via the bore of the male coupling 33 then passes through the passageway 26 of the valve actuator 24, through the ports 28 into the annular space 27, through the aperture 6 and into the first duct 3. The liquid is then conducted from the first duct 3 into the first conduit 29 so that liquid communication is thereby provided between the first and second conduits.

When it is required to discontinue the flow the male coupling 30 is uncoupled from the female coupling 23 and the valve actuator 24 returns to its rest position by action of the spring 8 as shown in FIG. 1 thereby closing the valve 9.

If infusion is to be discontinued for some time then the adaptor 12 is disconnected from the valve body 2. This disconnection disposes the planar end face 5 which can be swabbed clean. An exposed surface portion 34 of the valve member projects from the aperture and can also be swabbed clean. In this way the build-up of deposits with associated bacterial risk is avoided.

It is envisaged that the adaptor 12 would be regarded as a disposable item so that a new adaptor would be fitted with each subsequent connection of liquid supply.

Figure 3:
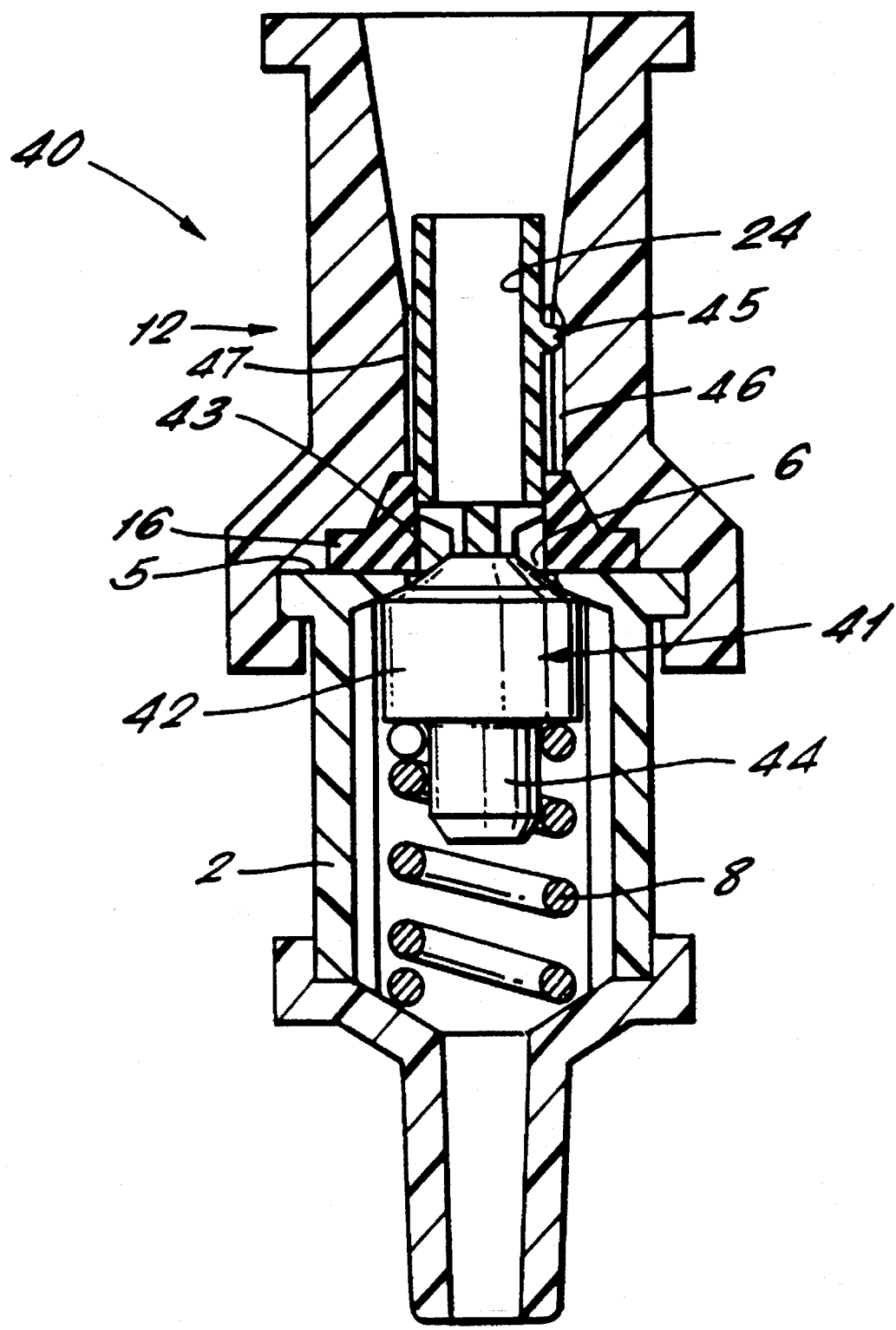
FIG. 3 is a longitudinal section of an alternative apparatus in accordance with the present invention showing the valve in the closed position prior to insertion of the male coupling.

An alternative apparatus 40 is shown in FIG. 3 and will be described using corresponding reference numerals to those of preceding Figures where appropriate for corresponding elements.

The apparatus 40 includes a valve body 2 and an adaptor 12 of similar proportions to those of the apparatus 1 and further includes an annular seal 16 and valve actuator 24 of like dimensions.

The apparatus 40 has a valve member 41 of elastomeric material having a cylindrical body 42 with a conically tapered valve face 43 which normally obturates the aperture 6 formed in the planar end face 5 of the valve body. The valve face 43 projects slightly from the aperture 6 and is thereby accessible for cleaning when the adaptor is disconnected from the valve body 2.

The valve member 41 has an axial projection 44 of reduced diameter about which the coil spring 8 is located.

The apparatus 40 operates in like manner to the apparatus 1, differing only in the shape of the valve member 41.

A further alternative apparatus 50 is shown in FIG. 4 which will be described using corresponding reference numerals to those of preceding figures where appropriate for corresponding elements.

The apparatus 50 has a valve body 2 in which male connector formations 18 are spaced axially from the end face 5 of the valve body. An adaptor 12 includes a cylindrical extension 51 having female connection formations 17 which are axially spaced forward of an end face 52 of the adaptor 12. The end face 52 is abutted by end face 5 of the body 2 when the adaptor 12 is connected to the body.

The cylindrical extension 51 is provided with an integrally formed first annular seal 53 which projects radially inwardly into sliding sealing contact with an external cylindrical surface 54 of the valve body 2. The first annular seal 53 is in the form of a tapered rib which is inclined relative to the axial extent of the cylindrical extension 51, the direction of inclination being such that the first annular seal tapers in a direction extending away from the end face 52.

The valve body 2 is provided with a chamfered edge 55 extending peripherally of the end face 5 to facilitate insertion of the valve body 2 within the adaptor 12 and in particular to allow progressive outward deformation of the first annular seal 53.

The apparatus 50 includes a valve actuator 24 which is provided with an integrally formed second annular seal 56 which projects radially outwardly into slidable sealing contact with a cylindrical bore surface 57 of a bore 58. The second annular seal 56 is in the form of a tapered rib inclined to the longitudinal axis of the actuator 24 in a direction towards the valve body 2. The bore 58 is stepped in diameter at a shoulder 59 such that a cylindrical bore extension 60 of reduced diameter communicates between the bore 58 and the second duct 13. Axial movement of the valve actuator 24 in a direction away from the end face 52 is limited by contact between the second annular seal 56 and the shoulder 59.

In use the adaptor 12 is coupled to the valve body 2 to which it is secured by action of the couplings 17 and 18. A male coupling of the type shown in FIG. 2 is coupled to the adaptor 12 such that an insertion member received within the second duct 13 urges the valve actuator 24 axially into engagement with spherical valve member 7. The leading end portion 25 bears against the valve member 7 which is depressed to a position in which the leading end portion projects through aperture 6 and fluid communication is established between the adaptor 12 and the valve body 2 in a similar manner to that described above with reference to FIG. 2.

The first annular seal 53 prevents the escape of liquid or the entry of air between the valve body 2 and the adaptor 12 and the second annular seal 56 similarly forms a seal between the adaptor 12 and the valve actuator 24.

The apparatus 50 has the advantage of not requiring the additional component of a resilient seal 16 of the type shown in FIGS. 1, 2 and 3. The need for radial projection 55 and groove 46 is also obviated by engagement between the shoulder 59 and the second annular seal 56 thereby simplifying construction.

The couplings and connectors of the apparatus may conveniently be of standard luer type or may be of any equivalent construction.

Apparatus in accordance with the present invention avoids the ingress of air during coupling of first and second conduits and because of the disposable nature of the adaptor it avoids problems associated with bacterial accumulation within residual infusate which can remain trapped within recesses in conventional apparatus for the same purpose.

Apparatus in accordance with the present invention as described above is particularly easy to use and provides a low cost solution to the requirements for coupling medical conduits.

What is claimed:

1. Apparatus for connecting medical conduits comprising a valve body defining a first duct and a mouth of the first duct, the valve body having first connecting means for connecting a first conduit in communication with the first duct and further comprising a valve having a valve member and biassing means which biases the valve member into position in which it closes the mouth of the first duct, an adaptor defining a second duct and a mouth of the second duct, the adaptor having a female coupling for connecting a second conduit having a co-operating male coupling in communication with the second duct, connector means, having two co-operatively connecting components, one of the connecting components peripherally engaging the valve body and the other of the connecting components peripherally engaging the adaptor, operable to releasably connect the valve body and the adaptor such that the mouth of the first duct is presented to the mouth of the second duct, and a valve actuator located within the second duct and movably engageable with the valve member when the valve body and adaptor are operatively connected, wherein the valve actuator is displaceable relative to the adaptor by insertion of the male coupling into operative engagement with the female coupling so as to move the valve member into a position in which the valve is opened, the actuator further comprising an integral annular seal member projecting radially into slidable sealing engagement with the adaptor and wherein the adaptor is provided with a bore receiving the actuator, the bore having a stepped diameter defining an annular shoulder co-operable with the annular seal member whereby the shoulder and the seal member constitute limiting means operable to limit travel of the actuator relative to the adaptor.

2. Apparatus as claimed in claim 1 wherein the valve member includes an exposed surface portion which, when the adaptor is separated from the valve body, is exposed via the mouth of the first duct and wherein the exposed surface portion is convex so as to project at least partially through the mouth of the first duct.

3. Apparatus as claimed in claim 2 wherein the valve member (7) is spherical.

4. Apparatus as claimed in claim 3 wherein the valve member (41) is formed of an elastomeric material.

5. Apparatus as claimed in claim 1 wherein the valve body comprises a first end having an end face and wherein the mouth of the first duct is formed in the end face, and wherein the end face is substantially free of projections and indentations.

6. Apparatus as claimed in claim 5 wherein the end face is planar.

7. Apparatus as claimed in claim 5 wherein the adaptor is provided with an annular seal operable to provide a continuous seal peripheral to the mouth of the first duct between the actuator and the end face of the valve body when the adaptor is connected to the body.

8. Apparatus as claimed in claim 7 wherein the seal is further operable to provide a continuous seal peripheral to the second duct between the actuator and the adaptor.

9. Apparatus as claimed in claim 1 comprising an annular seal member formed integrally with the adaptor and operable to provide a seal between an external cylindrical surface of the valve body and an internal cylindrical surface of the adaptor.

10. An apparatus as claimed in claim 9, wherein:
   the valve member is spherical, has an exposed portion which, when the adaptor is separated from the valve body, is exposed via the mouth of the first duct and wherein the exposed surface portion is convex so as to project at least partially through the mouth of the first duct and is formed from an elastomeric material;
   the valve body comprises a first end having a planar end face and wherein the mouth of the first duct is formed in the end face, and wherein the end face is substantially free of projections and indentations; and
   the adaptor is provided with an annular seal operable to provide a continuous seal peripheral to the mouth of the first duct between the actuator and the end face of the valve body when the adaptor is connected to the body, the seal further operable to provide a continuous seal peripheral to the second duct between the actuator and the adaptor.

* * * * *